US010557121B2

(12) United States Patent
Tsumaki

(10) Patent No.: US 10,557,121 B2
(45) Date of Patent: Feb. 11, 2020

(54) METHOD FOR CHONDROGENIC INDUCTION

(71) Applicant: Kyoto University, Kyoto (JP)

(72) Inventor: Noriyuki Tsumaki, Kyoto (JP)

(73) Assignee: Kyoto University, Kyoto (JP)

( * ) Notice: Subject to any disclaimer, the term of this patent is extended or adjusted under 35 U.S.C. 154(b) by 197 days.

(21) Appl. No.: 15/552,156

(22) PCT Filed: Feb. 19, 2016

(86) PCT No.: PCT/JP2016/054917
§ 371 (c)(1),
(2) Date: Aug. 18, 2017

(87) PCT Pub. No.: WO2016/133208
PCT Pub. Date: Aug. 25, 2016

(65) Prior Publication Data
US 2018/0251732 A1 Sep. 6, 2018

(30) Foreign Application Priority Data
Feb. 19, 2015 (JP) .................. 2015-030168

(51) Int. Cl.
| C12N 5/00 | (2006.01) |
| C12N 5/02 | (2006.01) |
| C12N 5/077 | (2010.01) |
| A61P 19/04 | (2006.01) |
| A61K 35/35 | (2015.01) |
| A61L 27/38 | (2006.01) |
| A61L 27/54 | (2006.01) |

(52) U.S. Cl.
CPC ............ *C12N 5/0655* (2013.01); *A61K 35/35* (2013.01); *A61L 27/3817* (2013.01); *A61L 27/54* (2013.01); *A61P 19/04* (2018.01); *A61L 2300/412* (2013.01); *A61L 2300/64* (2013.01); *A61L 2430/06* (2013.01); *C12N 2501/15* (2013.01); *C12N 2501/155* (2013.01); *C12N 2501/19* (2013.01); *C12N 2501/71* (2013.01); *C12N 2506/45* (2013.01)

(58) Field of Classification Search
CPC ...................... C12N 5/0655; C12N 2501/15
USPC ................................. 435/325, 377
See application file for complete search history.

(56) References Cited

FOREIGN PATENT DOCUMENTS

| EP | 3 064 577 A1 | 9/2016 |
| EP | 3 078 387 A1 | 10/2016 |
| JP | 2011-41472 A | 3/2011 |
| WO | WO 2011/066403 A1 | 6/2011 |
| WO | WO 2015/064754 A1 | 5/2015 |
| WO | WO 2015/083582 A1 | 6/2015 |

OTHER PUBLICATIONS

Vosogh (2013, Stem Cells and Development, 22:2693-2705).*
Steiner (2010, Nature Biotechnology, 28:pp. 361-365).*
International Preliminary Report on Patentability for PCT/JP2016/054917 dated Aug. 22, 2017.
Bai, Hai Yan et al., "Three step derivation of cartilage like tissue from human embryonic stem cells by 2D-3D sequential culture in vitro and further implantation in vivo on alginate/PLGA scaffolds" Journal of Biomedical Materials Research, Aug. 2010, pp. 539-546, vol. 94A, Issue 2.
Hwang, Nathaniel S. et al., "Derivation of Chondrogenically-Committed Cells from Human Embryonic Cells for Cartilage Tissue Regeneration" PLoS ONE, Jun. 2008, pp. 1-10, vol. 3, Issue 6, e2498.
Koyama, Noriaki et al., "Human Induced Pluripotent Stem Cells Differentiated into Chondrogenic Lineage Via Generation of Mesenchymal Progenitor Cells" Stem Cells and Development, Jan. 2013, pp. 102-113, vol. 22, No. 1—Abstract
Mithoefer, Kai et al., "Clinical Efficacy of the Microfracture Technique for Articular Cartilage Repair in the Knee" The American Journal of Sports Medicine, 2009, pp. 2053-2063, vol. 37, No. 10.
Oldershaw, Rachel A. et al., "Directed differentiation of human embryonic stem cells toward chondrocytes" Nature Biotechnology, Nov. 2010, pp. 1187-1194, vol. 28, No. 11.
Roberts, S. et al., "Immunohistochemical study of collagen types I and II and procollagen IIA in human cartilage repair tissue following autologous chondrocyte implantation" The Knee, 2009, pp. 398-404, vol. 16.
Yamashita, Akihiro et al., "Cartilage tissue engineering identifies abnormal human induced pluripotent stem cells" Scientific Reports, 2013, pp. 1-6, vol. 3, Article No. 1978.
Yamashita, A. et al., "Statin treatment rescues FGFR3 skeletal dysplasia phenotypes" Nature, Sep. 2014, pp. 507-511, vol. 513.
International Search Report for PCT/JP2016/054917 dated May 24, 2016.
Murphy, Meghan K. et al., "TGF-β1, GDF-5, and BMP-2 Stimulation Induces Chondrogenesis in Expanded Human Articular Chondrocytes and Marrow-Derived Stromal Cells" Stem Cells, 2015, pp. 762-773, vol. 33.
Tsumaki, Noriyuki et al., "iPS cell technologies and cartilage regeneration" Bone, 2015, pp. 48-54, vol. 70.
Supplementary European Search Report for EP 16752594 dated Aug. 29, 2018.

* cited by examiner

*Primary Examiner* — Valarie E Bertoglio
(74) *Attorney, Agent, or Firm* — Knobbe Martens Olson & Bear LLP

(57) ABSTRACT

Provided is a method for producing chondrocytes from pluripotent stem cells, the method comprising the steps of:
(i) culturing pluripotent stem cells under adherent conditions in a medium containing an HMG-CoA reductase inhibitor and one or more substances selected from the group consisting of BMP2, TGFβ and GDF5, and
(ii) culturing the cells obtained in step (i) under suspension conditions in a medium containing an HMG-CoA reductase inhibitor and one or more substances selected from the group consisting of BMP2, TGFβ and GDF5.
Also provided is a pharmaceutical product comprising chondrocytes obtained by the method.

9 Claims, 4 Drawing Sheets

Scale bars 50 μm

Human iPS cell-derived cartilage

Mouse embryonic cartilage primordium (humerus)

Subcutaneous transplantation of hiPSC-derived cartilage into SCID mice 3 months post-transplantation 12 months post-transplantation

METHOD FOR CHONDROGENIC INDUCTION

CROSS REFERENCE TO RELATED APPLICATIONS

This application is a U.S. National Phase Application of PCT International Application Number PCT/JP2016/054917, filed on Feb. 19, 2016, designating the United States of America and published in Japanese, which is an International Application of and claims the benefit of priority to Japanese Patent Application No. 2015-030168, filed on Feb. 19, 2015. The disclosures of the above-referenced applications are hereby expressly incorporated by reference in their entireties.

TECHNICAL FIELD

The present invention relates to a method for inducing pluripotent stem cells to differentiate into chondrocytes. The present invention also relates to a therapeutic agent comprising chondrocytes produced by the method.

BACKGROUND ART

Cartilage tissue is a component of the nose, ears and joints. Cartilage tissue is composed of chondrocytes and a specific extracellular matrix that contains type II, IX, and XI collagens and proteoglycans, but not type I collagen. Cartilage tissue damaged by joint injury etc. does not spontaneously heal itself, and the damage will deteriorate without repair treatment such as transplantation. For transplantation, however, cartilage tissue to be transplanted into the damaged site needs to be obtained. Transplantation of the patient's own cartilage from other body parts inevitably results in lack of cartilage tissue in these parts, and therefore, the size of the damage site that can be treated by transplantation is limited. Another current approach is transplantation of the expansion culture product of harvested chondrocytes, but chondrocytes may be transformed into fibroblastic cells during in vitro culture and this approach cannot produce a sufficient therapeutic effect (Non Patent Literature 1). Yet another proposed treatment is administration of mesenchymal stem cells. However, mesenchymal stem cells can differentiate into multiple types of cells, and the administration inevitably results in transplantation of not only chondrocytes but also undesirable tissues, such as fibrous tissue expressing type I collagen and hypertrophic tissue expressing type X collagen (Non Patent Literature 2).

Currently proposed is repair treatment using chondrocytes induced from pluripotent stem cells, such as iPS and ES cells (Non Patent Literature 3 to 7). However, the use of pluripotent stem cells has produced several problems, including the formation of fibrocartilage and teratoma. Therefore, there is a need for the development of a method for driving pluripotent stem cells to generate high-quality cartilage tissue without in vivo cancer formation.

CITATION LIST

Non Patent Literature

Non Patent Literature 1: Roberts, S., et al. Knee 16, 398-404 (2009).
Non Patent Literature 2: Mithoefer, K., et al. Am. J. Sports Med. 37, 2053-2063 (2009).
Non Patent Literature 3: Koyama, N. et al. Stem cells and development 22, 102-113 (2013).
Non Patent Literature 4: Hwang, N. S., et al. PLoS ONE 3, e2498 (2008).
Non Patent Literature 5: Oldershaw, R. A. et al. Nat. Biotechnol. 28, 1187-1194 (2010).
Non Patent Literature 6: Bai, H. Y., et al. Journal of biomedical materials research. Part A 94, 539-546 (2010).
Non Patent Literature 7: Yamashita, A. et al. Scientific Reports 3 (2013).

SUMMARY OF INVENTION

Technical Problem

An object of the present invention is to provide a method for inducing pluripotent stem cells to differentiate into chondrocytes. In particular, an object of the present invention is to provide a method for stably inducing chondrogenic differentiation in simple steps.

Solution to Problem

The present inventor conducted extensive research to solve the above-described problems, and as a result, found that a combination of adherent culture and suspension culture of pluripotent stem cells in a medium containing an HMG-CoA reductase inhibitor can stably produce chondrocytes. Based on this finding, the present invention was completed.

That is, the present invention includes the following.
(1) A method for producing chondrocytes from pluripotent stem cells, the method comprising the steps of:
(i) culturing pluripotent stem cells under adherent conditions in a medium containing an HMG-CoA reductase inhibitor and one or more substances selected from the group consisting of BMP2, TGFβ and GDF5, and
(ii) culturing the cells obtained in step (i) under suspension conditions in a medium containing an HMG-CoA reductase inhibitor and one or more substances selected from the group consisting of BMP2, TGFβ and GDF5.
(2) The method according to the above (1), wherein the medium used in steps (i) and (ii) is a medium containing BMP2, TGFβ, GDF5 and a HMG-CoA reductase inhibitor.
(3) The method according to the above (1) or (2), wherein the HMG-CoA reductase inhibitor is selected from the group consisting of mevastatin, atorvastatin, pravastatin, rosuvastatin, fluvastatin and lovastatin.
(4) The method according to the above (3), wherein the HMG-CoA reductase inhibitor is rosuvastatin.
(5) The method according to any one of the above (1) to (4), wherein the medium used in steps (i) and (ii) further contains serum.
(6) The method according to any one of the above (1) to (5), wherein step (ii) is a step of culturing the cells obtained in step (i) in suspension without use of a detachment solution.
(7) The method according to any one of the above (1) to (6), wherein the pluripotent stem cells used in step (i) are in the form of cell clusters.
(8) The method according to the above (7), wherein the pluripotent stem cells are in the form of cell clusters produced by a method comprising a step of suspension culture in a medium that allows the pluripotent stem cells to retain their undifferentiated state.
(9) The method according to any one of the above (1) to (8), wherein the chondrocytes are in the form of clusters containing the chondrocytes and an extracellular matrix.

(10) The method according to any one of the above (1) to (9), wherein steps (i) and (ii) each take 7 to 28 days.
(11) The method according to the above (10), wherein steps (i) and (ii) each take 14 days.
(12) A pharmaceutical product comprising chondrocytes produced by the method according to any of the above (1) to (11).
(13) The pharmaceutical product according to the above (12) for use in treatment of articular cartilage injury.

Advantageous Effects of Invention

The present invention is the first to achieve stable induction of differentiation of pluripotent stem cells (e.g., iPS cells) into high-quality chondrocytes in simple steps. The chondrocytes produced by the method of the present invention can be used for regenerative medicine for cartilage.

DESCRIPTION OF EMBODIMENTS

Figure 1:
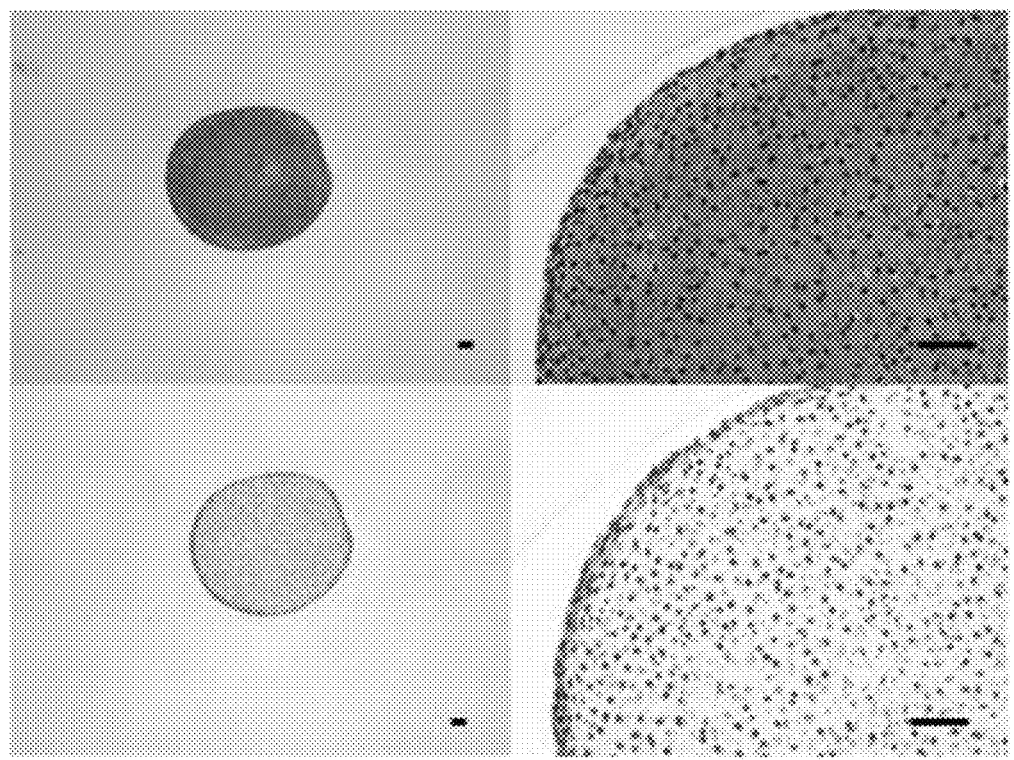
FIG. 1 shows the images of HE staining and safranin O staining of a particle harvested after 28 days of differentiation induction of human iPS cell clusters in chondrogenic differentiation medium.

The present invention will be described in detail below.
The present invention provides a method for producing chondrocytes from pluripotent stem cells, which method comprises the following steps:
(i) culturing pluripotent stem cells under adherent conditions in a medium containing an HMG-CoA reductase inhibitor and one or more substances selected from the group consisting of BMP2, TGFβ and GDF5, and
(ii) culturing the cells obtained in step (i) under suspension conditions in a medium containing an HMG-CoA reductase inhibitor and one or more substances selected from the group consisting of BMP2, TGFβ and GDF5.

Pluripotent stem cells that can be used in the present invention are stem cells having both pluripotency, by which the cells are capable of differentiating into any types of cells in the body, and proliferation potency. Examples of the pluripotent stem cells include, but are not limited to, embryonic stem (ES) cells, embryonic stem cells from clone embryos obtained by nuclear transplantation (nuclear transfer ES (ntES) cells), spermatogonial stem cells (germline stem (GS) cells), embryonic germ cells (EG cells), induced pluripotent stem (iPS) cells and pluripotent cells (Muse cells) derived from cultured fibroblasts or myeloid stem cells. Preferred pluripotent stem cells are ES cells, ntES cells and iPS cells.

(A) Embryonic Stem Cells

ES cells are stem cells having pluripotency and proliferation potency via self-replication, and are established from the inner cell mass of early embryos (e.g., blastocysts) of a mammal such as a human and a mouse.

ES cells are stem cells derived from the inner cell mass of a blastocyst, an embryo that has developed beyond the morula and eight-cell stages from a fertilized egg. ES cells have so-called pluripotency, by which they are capable of differentiating into any types of cells composing an adult body, and proliferation potency via self-replication. ES cells were discovered in mice in 1981 (M. J. Evans and M. H. Kaufman (1981), Nature 292:154-156). Thereafter, ES cell lines were established in primates including humans, monkeys, etc. (J. A. Thomson et al. (1998), Science 282:1145-1147; J. A. Thomson et al. (1995), Proc. Natl. Acad. Sci. USA, 92:7844-7848; J. A. Thomson et al. (1996), Biol. Reprod., 55:254-259; J. A. Thomson and V. S. Marshall (1998), Curr. Top. Dev. Biol., 38:133-165).

ES cells can be established by harvesting the inner cell mass from blastocysts developed from fertilized eggs of a subject animal and then culturing the inner cell mass on fibroblasts as feeders. Cell maintenance by subculture can be performed using a medium supplemented with substances such as leukemia inhibitory factor (LIF) and basic fibroblast growth factor (bFGF). Methods for establishment and maintenance of human and monkey ES cells are described in, for example, U.S. Pat. No. 5,843,780; Thomson J A, et al. (1995), Proc Natl. Acad. Sci. USA. 92:7844-7848; Thomson J A, et al. (1998), Science. 282:1145-1147; H. Suemori et al. (2006), Biochem. Biophys. Res. Commun., 345:926-932; M. Ueno et al. (2006), Proc. Natl. Acad. Sci. USA, 103:9554-9559; H. Suemori et al. (2001), Dev. Dyn., 222:273-279; H. Kawasaki et al. (2002), Proc. Natl. Acad. Sci. USA, 99:1580-1585; Klimanskaya I, et al. (2006), Nature. 444:481-485; etc.

Human ES cells can be maintained under a humid atmosphere of 2% $CO_2$/98% air at 37° C. in a medium for preparation of ES cells, for example, a DMEM/F-12 medium supplemented with 0.1 mM 2-mercaptoethanol, 0.1 mM non-essential amino acids, 2 mM L-glutamic acid, 20% KSR and 4 ng/mL bFGF (O. Fumitaka et al. (2008), Nat. Biotechnol., 26:215-224). ES cells need to be subcultured every 3 to 4 days. The subculture can be performed using, for example, 0.25% trypsin and 0.1 mg/mL collagenase IV in PBS containing 1 mM $CaCl_2$ and 20% KSR.

ES cells can be generally selected by using the expression of gene markers as an index, such as alkaline phosphatase, Oct-3/4 and Nanog. The markers can be detected by real-time PCR. In particular, for selection of human ES cells, the expression of gene markers such as OCT-3/4, NANOG and ECAD can be used as an index (E. Kroon et al. (2008), Nat. Biotechnol., 26:443-452).

Human ES cell lines, for example, WA01 (H1) and WA09 (H9) are available from WiCell Research Institute, Inc., and KhES-1, KhES-2 and KhES-3 are available from the Institute for Frontier Medical Sciences, Kyoto University (Kyoto, Japan).

(B) Spermatogonial Stem Cells

Spermatogonial stem cells are testis-derived pluripotent stem cells, serving as an origin for spermatogenesis. As with ES cells, spermatogonial stem cells can also be induced to differentiate into cells of various lineages. For example, the transplantation of spermatogonial stem cells into mouse blastocysts can generate chimeric mice (M. Kanatsu-Shinohara et al. (2003) Biol. Reprod., 69:612-616; K. Shinohara et al. (2004), Cell, 119:1001-1012). In addition, spermatogonial stem cells are self-replicable in a medium containing glial cell line-derived neurotrophic factor (GDNF), and spermatogonial stem cells can be obtained by repeated subculture under culture conditions similar to those for ES cell establishment (Masanori Takebayashi et al., (2008), Experimental Medicine, Vol. 26, No. 5 (Extra Number), pp. 41-46, YODOSHA (Tokyo, Japan)).

(C) Embryonic Germ Cells

Embryonic germ cells are cells established from primordial germ cells at the embryonic period and have pluripotency like ES cells. Embryonic germ cells can be established by culturing primordial germ cells in the presence of substances such as LIF, bFGF and stem cell factor (Y. Matsui et al. (1992), Cell, 70:841-847; J. L. Resnick et al. (1992), Nature, 359:550-551).

(D) Induced Pluripotent Stem Cells

Induced pluripotent stem (iPS) cells can be generated by introducing specific reprogramming factors in the form of DNA or protein into somatic cells. iPS cells are somatic cell-derived artificial stem cells having almost the same properties as those of ES cells, such as pluripotency and proliferation potency via self-replication (K. Takahashi and S. Yamanaka (2006) Cell, 126:663-676; K. Takahashi et al. (2007), Cell, 131:861-872; J. Yu et al. (2007), Science, 318:1917-1920; Nakagawa, M. et al., Nat. Biotechnol. 26:101-106 (2008); WO 2007/069666). The reprogramming factor may be a gene specifically expressed in ES cells, a gene product or non-coding RNA thereof, a gene playing an important role in the maintenance of the undifferentiated state of ES cells, a gene product or non-coding RNA thereof, or a low-molecular-weight compound. Examples of the genes serving as the reprogramming factors include, for example, Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, β-catenin, Lin28b, Sall1, Sall4, Esrrb, Nr5a2, Tbx3 and Glis1. One of these reprogramming factors may be used alone, and also two or more of them may be used in combination. Examples of the combination of such reprogramming factors include those described in WO 2007/069666, WO 2008/118820, WO 2009/007852, WO 2009/032194, WO 2009/058413, WO 2009/057831, WO 2009/075119, WO 2009/079007, WO 2009/091659, WO 2009/101084, WO 2009/101407, WO 2009/102983, WO 2009/114949, WO 2009/117439, WO 2009/126250, WO 2009/126251, WO 2009/126655, WO 2009/157593, WO 2010/009015, WO 2010/033906, WO 2010/033920, WO 2010/042800, WO 2010/050626, WO 2010/056831, WO 2010/068955, WO 2010/098419, WO 2010/102267, WO 2010/111409, WO 2010/111422, WO 2010/115050, WO 2010/124290, WO 2010/147395, WO 2010/147612, Huangfu D, et al. (2008), Nat. Biotechnol., 26:795-797, Shi Y, et al. (2008), Cell Stem Cell, 2:525-528, Eminli S, et al. (2008), Stem Cells. 26:2467-2474, Huangfu D, et al. (2008), Nat Biotechnol. 26:1269-1275, Shi Y, et al. (2008), Cell Stem Cell, 3, 568-574, Zhao Y, et al. (2008), Cell Stem Cell, 3:475-479, Marson A, (2008), Cell Stem Cell, 3, 132-135, Feng B, et al. (2009), Nat Cell Biol. 11:197-203, R. L. Judson et al., (2009), Nat. Biotech., 27:459-461, Lyssiotis C A, et al. (2009), Proc Natl Acad Sci USA. 106:8912-8917, Kim J B, et al. (2009), Nature. 461:649-643, Ichida J K, et al. (2009), Cell Stem Cell. 5:491-503, Heng J C, et al. (2010), Cell Stem Cell. 6:167-74, Han J, et al. (2010), Nature. 463:1096-100, Mali P, et al. (2010), Stem Cells. 28:713-720, and Maekawa M, et al. (2011), Nature. 474:225-9.

The reprogramming factors also include factors used for enhancing the establishment efficiency, such as histone deacetylase (HDAC) inhibitors [e.g., low-molecular-weight inhibitors such as valproic acid (VPA), trichostatin A, sodium butyrate, MC 1293 and M344, and nucleic acid-based expression inhibitors such as siRNA and shRNA against HDAC (e.g., HDAC1 siRNA Smartpool (Millipore), HuSH 29-mer shRNA Constructs against HDAC1 (OriGene), etc.)], MEK inhibitors (e.g., PD184352, PD98059, U0126, SL327 and PD0325901), glycogen synthase kinase-3 inhibitors (e.g., Bio and CHIR99021), DNA methyltransferase inhibitors (e.g., 5-azacytidine), histone methyltransferase inhibitors (e.g., low-molecular-weight inhibitors such as BIX-01294, and nucleic acid-based expression inhibitors such as siRNA and shRNA against Suv39h1, Suv39h2, SetDB1 or G9a), L-channel calcium agonists (e.g., Bayk8644), butyric acid, TGFβ inhibitors or ALK5 inhibitors (e.g., LY364947, SB431542, 616453 and A-83-01), p53 inhibitors (e.g., siRNA and shRNA against p53), ARID3A inhibitors (e.g., siRNA and shRNA against ARID3A), miR-NAs such as miR-291-3p, miR-294, miR-295 and mir-302, Wnt signaling (e.g., soluble Wnt3a), neuropeptide Y, prostaglandins (e.g., prostaglandin E2 and prostaglandin J2), hTERT, SV40LT, UTF1, IRX6, GLIS1, PITX2, DMRTB1, etc. These factors used for enhancing the establishment efficiency are not distinguished from the reprogramming factors in the present invention.

The reprogramming factors may be introduced in the form of protein into somatic cells by a technique such as lipofection, fusion with a cell membrane-permeable peptide (e.g., HIV TAT and polyarginine) and microinjection.

Alternatively, the reprogramming factors may be introduced in the form of DNA into somatic cells by a technique such as a technique using a vector (such as a viral vector, a plasmid vector and an artificial chromosome vector), lipofection, a technique using a liposome and microinjection. Examples of the viral vector include retroviral vectors, lentiviral vectors (both described in Cell, 126, pp. 663-676, 2006; Cell, 131, pp. 861-872, 2007; Science, 318, pp. 1917-1920, 2007), adenoviral vectors (Science, 322, 945-949, 2008), adeno-associated viral vectors and Sendai virus vectors (WO 2010/008054). Examples of the artificial chromosome vector include human artificial chromosome (HAC) vectors, yeast artificial chromosome (YAC) vectors and bacterial artificial chromosome (BAC, PAC) vectors. Examples of the plasmid vector include plasmids for mammalian cells (Science, 322:949-953, 2008). Such a vector can contain regulatory sequences such as a promoter, an enhancer, a ribosome binding sequence, a terminator and a polyadenylation site, so that a nuclear reprogramming factor can be expressed. The vector may further contain, if necessary, a selection marker sequence such as a drug resistance gene (e.g., a kanamycin resistance gene, an ampicillin resistance gene and a puromycin resistance gene), a thymidine kinase gene and a diphtheria toxin gene; a reporter gene sequence such as a green fluorescent protein (GFP), β-glucuronidase (GUS) and FLAG; and/or other sequences. In order to remove a gene encoding a reprogramming factor or remove a promoter together with a gene encoding a reprogramming factor binding thereto after introduction of the vector into somatic cells, LoxP sequences may be inserted upstream and downstream of the region to be removed.

Alternatively, the reprogramming factors may be introduced in the form of RNA into somatic cells by a technique such as lipofection and microinjection. In order to prevent decomposition, RNAs containing 5-methylcytidine and pseudouridine (TriLink BioTechnologies) may be used (Warren L (2010), Cell Stem Cell. 7:618-630).

The culture medium for iPS cell generation is, for example, DMEM, DMEM/F12 or DME medium containing 10 to 15% FBS (these media may further contain LIF, penicillin/streptomycin, puromycin, L-glutamine, non-essential amino acids, β-mercaptoethanol, etc. as needed), or a commercially available medium such as a medium for mouse ES cell culture (e.g., TX-WES medium (Thromb-X)), a medium for primate ES cell culture (e.g., a medium for primate ES/iPS cells (ReproCELL)) and a serum-free medium for maintenance of pluripotent stem cells (e.g., mTeSR (STEMCELL Technologies), Essential 8 (Life Technologies) and StemFit AK03 (AJINOMOTO)).

An exemplary culture method is as follows. Somatic cells are brought into contact with reprogramming factors in a DMEM or DMEM/F12 medium containing 10% FBS at 37° C. in an atmosphere of 5% $CO_2$ and then cultured for about 4 to 7 days. The cells are then reseeded on feeder cells (e.g., mitomycin C-treated STO cells, SNL cells, etc.). About 10 days after contact between the somatic cells and the reprogramming factors, the medium is changed to a bFGF-containing medium for primate ES cell culture, and cell culture is continued. About 30 to 45 days or more after the contact, iPS cell-like colonies appear.

Alternatively, the cells are cultured on feeder cells (e.g., mitomycin C-treated STO cells, SNL cells, etc.) in a 10% FBS-containing DMEM medium (this medium may further contain LIF, penicillin/streptomycin, puromycin, L-glutamine, non-essential amino acids, β-mercaptoethanol, etc. as needed) at 37° C. in an atmosphere of 5% $CO_2$. About 25 to 30 days or more after the start of culture, ES-like colonies appear. Preferably, instead of feeder cells, the somatic cells to be reprogrammed are used as feeder cells (Takahashi K, et al. (2009), PLoS One. 4:e8067, or WO 2010/137746), or alternatively, an extracellular matrix (e.g., laminin-5 (WO 2009/123349) and Matrigel (BD)) is used.

Alternatively, the cells may be cultured in a serum-free medium (Sun N, et al. (2009), Proc Natl Acad Sci USA. 106:15720-15725). For enhancing the establishment efficiency of iPS cells, low oxygen conditions (oxygen concentration of 0.1 to 15%) may be employed (Yoshida Y, et al. (2009), Cell Stem Cell. 5:237-241, or WO 2010/013845).

During the above culture, medium change to a fresh medium is performed once a day after day 2 of the culture. The number of somatic cells to undergo nuclear reprogramming is not limited, and for example, ranges from about $5 \times 10^3$ to $5 \times 10^6$ cells per culture dish (100 $cm^2$).

iPS cells can be selected based on the shape of the colonies. When a drug resistance gene to be expressed along with the gene expressed during somatic cell reprogramming (e.g., Oct3/4, Nanog) is introduced as a marker gene, established iPS cells can be selected by culturing the cells in a medium containing the relevant drug (selective medium). When a fluorescent protein gene is used as a marker gene, iPS cells of interest can be selected by observation under a fluorescence microscope. When a luminescent enzyme gene is used as a marker gene, iPS cells of interest can be selected by adding a luminescent substrate. When a chromogenic enzyme gene is used as a marker gene, iPS cells of interest can be selected by adding a chromogenic substrate.

The term "somatic cells" as used herein refers to any types of animal cells (preferably mammalian cells including human cells) other than germ cells or totipotent cells such as ova, oocytes and ES cells. Somatic cells include, but are not limited to, somatic cells of fetuses, somatic cells of neonates, and mature healthy or pathogenic somatic cells, as well as primary cultured cells, passaged cells and established cell lines. Specific examples of the somatic cells include (1) tissue stem cells (somatic stem cells), such as neural stem cells, hematopoietic stem cells, mesenchymal stem cells and dental pulp stem cells,
(2) tissue progenitor cells, and
(3) differentiated cells, such as lymphocytes, epithelial cells, endothelial cells, muscle cells, fibroblasts (skin cells etc.), hair cells, hepatocytes, gastric mucosal cells, enterocytes, splenocytes, pancreatic cells (pancreatic exocrine cells etc.), brain cells, lung cells, renal cells and adipocytes.

When iPS cells are used to generate cells to be transplanted, the iPS cells are preferably produced from somatic cells having the same or substantially the same HLA alleles as those of the recipient to prevent rejection. The term "substantially the same" herein means that the HLA alleles match to the extent that immune response against the transplanted cells can be inhibited by an immunosuppressant. The somatic cells have, for example, three matched HLA alleles including HLA-A, HLA-B and HLA-DR or four matched HLA alleles further including HLA-C.

(E) ES Cells Derived from Clone Embryos Generated by Nuclear Transplantation ntES (nuclear transfer ES) cells are ES cells derived from clone embryos generated by nuclear transplantation techniques, and have almost the same properties as those of fertilized egg-derived ES cells (T. Wakayama et al. (2001), Science, 292:740-743; S. Wakayama et al. (2005), Biol. Reprod., 72:932-936; J. Byrne et al. (2007), Nature, 450: 497-502). Specifically, ntES cells are ES cells established from the blastocyst inner cell mass of a clone embryo obtained via replacement of the nucleus of an unfertilized egg with the nucleus of a somatic cell. For preparation of ntES cells, nuclear transplantation techniques (J. B. Cibelli et al. (1998), Nature Biotechnol., 16:642-646) and the above ES cell preparation techniques are used in combination (Kiyoka Wakayama et al., (2008), Experimental Medicine, Vol. 26, No. 5 (Extra Number), pp. 47-52). In nuclear transplantation, the nucleus of a somatic cell is injected into a mammalian enucleated unfertilized egg and then the resulting cell is cultured for several hours so as to undergo reprogramming.

(F) Multilineage-Differentiating Stress Enduring Cells (Muse Cells)

Muse cells are pluripotent stem cells produced by the method described in WO 2011/007900. Specifically, Muse cells are pluripotent cells produced by subjecting fibroblasts or bone marrow stromal cells to trypsin treatment for a long period of time, preferably 8 or 16 hours, and then culturing the cells in suspension. Muse cells are SSEA-3 and CD105 positive.

The pluripotent stem cells used for the production of chondrocytes in the present invention are preferably maintained in three-dimensional suspension culture to form cell clusters while retaining their undifferentiated state until the subsequent induction step. The three-dimensional suspension culture in the present invention is a culture method in which cells are cultured with stirring or agitation in medium under non-adherent conditions.

In the cell clusters of more than 300 μm in diameter, cytokines etc. secreted by cells in the clusters may induce cell differentiation and necrosis may occur inside the cell clusters. For these reasons, the diameter of the cell clusters needs to be adjusted to not more than 300 μm. The adjustment of the diameter of the cell clusters can be achieved by, for example, appropriately adjusting cell density and stirring speed and/or sieving cell clusters through a mesh. The mesh used here is not particularly limited and may be any sterilizable mesh. The examples include a nylon mesh and a metal mesh such as a stainless mesh.

The medium used in the three-dimensional suspension culture of pluripotent stem cells in the present invention is not particularly limited and may be any medium that allows pluripotent stem cells to retain their undifferentiated state. Examples of such a medium include DMEM/F12 or DMEM containing 10 to 15% FBS (these media may further contain LIF, penicillin/streptomycin, puromycin, L-glutamine, non-essential amino acids, β-mercaptoethanol, etc. as needed), and commercially available media such as a medium for mouse ES cell culture (e.g., TX-WES medium (Thromb-X)), a medium for primate ES cell culture (e.g., a medium for primate ES/iPS cells (ReproCELL)) and a serum-free medium for maintenance of pluripotent stem cells (e.g., mTeSR (STEMCELL Technologies), Essential 8 (Life Technologies) and StemFit AK03 (AJINOMOTO)).

The medium used in the three-dimensional suspension culture of pluripotent stem cells in the present invention may further contain a ROCK inhibitor for prevention of cell death. The ROCK inhibitor is not particularly limited and may be any substance that can inhibit the function of Rho-kinase (ROCK). The examples include Y-27632 (see, for example, Ishizaki et al., Mol. Pharmacol. 57, 976-983 (2000); and Narumiya et al., Methods Enzymol. 325, 273-284 (2000)), Fasudil/HA1077 (see, for example, Uenata et al., Nature 389:990-994 (1997)), H-1152 (see, for example, Sasaki et al., Pharmacol. Ther. 93:225-232 (2002)), Wf-536 (see, for example, Nakajima et al., Cancer Chemother Pharmacol. 52(4):319-324 (2003)) and derivatives of the foregoing; and further include an antisense nucleic acid against ROCK, a nucleic acid capable of inducing RNA interference (e.g., siRNA) targeting ROCK, a dominant negative mutant of ROCK, and expression vectors for the foregoing. In addition, other low-molecular-weight compounds known as a ROCK inhibitor can be used (see, for example, U.S. Patent Publication Nos. 2005/0209261, 2005/0192304, 2004/0014755, 2004/0002508, 2004/0002507, 2003/0125344 and 2003/0087919; and WO 2003/062227, WO 2003/059913, WO 2003/062225, WO 2002/076976 and WO 2004/039796). In the present invention, one or more kinds of ROCK inhibitors may be used. Preferable examples of the ROCK inhibitor used in this step include Y-27632. The concentration of the ROCK inhibitor used in this step can be selected by those skilled in the art as appropriate for the ROCK inhibitor to be used. For example, when Y-27632 is used as the ROCK inhibitor, the concentration is 0.1 μM to 100 μM, preferably 1 μM to 50 μM, more preferably 5 μM to 20 μM.

The medium used in the three-dimensional suspension culture of pluripotent stem cells in the present invention may further contain a reagent for preventing the adhesion between cell clusters or a reagent for maintaining the suspension state of cell clusters. Such a reagent is, for example, a water-soluble polymer, preferably a water-soluble polysaccharide (e.g., methylcellulose and gellan gum).

The culture vessel used in the three-dimensional suspension culture is not particularly limited and may be any non-adherent culture vessel. The examples include a bioreactor, a flask, a tissue culture flask, a dish, a Petri dish, a tissue culture dish, a multidish, a microplate, a microwell plate, a multiplate, a multiwell plate, a chamber slide, a culture dish, a tube, a tray, a culture bag and a roller bottle. Such a culture vessel may be equipped with a stirring device and/or an air supply system as appropriate. In the case where the culture vessel is made of a gas permeable material or equipped with a stirring device in which the stirring blade is adjusted in size and shape to generate an axial stream on the surface of the fluid in the culture vessel, no air supply system is needed. A preferable example of the culture vessel used in the three-dimensional suspension culture in the present invention is a bioreactor with a magnetic stirrer manufactured by ABLE Corporation.

When a culture vessel equipped with a stirring device is used in the three-dimensional suspension culture, the stirring speed is not particularly limited as long as the cells can be maintained in a suspension state, and is for example, 30 rpm to 80 rpm, preferably 40 rpm to 70 rpm, more preferably 50 rpm to 60 rpm.

The cell density in the three-dimensional suspension culture is for example $1.0 \times 10^4$ cells/mL to $1.0 \times 10^6$ cells/mL, preferably $3.0 \times 10^4$ cells/mL to $1.0 \times 10^5$ cells/mL. The adjustment to a desired cell number can be achieved by increasing or decreasing the volume of the medium as appropriate.

The culture temperature in the three-dimensional suspension culture is not particularly limited, and is for example, about 30 to 40° C., preferably about 37° C. The culture is performed under an atmosphere of air with $CO_2$. The $CO_2$ concentration is about 2 to 5%, preferably about 5%. The culture period in this step is not particularly limited as long as the diameter of the cell clusters is maintained within 300 μm during the culture period, and is for example, 3 to 10 days, preferably 4 to 7 days, preferably 5 days.

The term "chondrocytes" used herein refers to cells that produce an extracellular matrix (such as collagen), a component of cartilage, or refers to progenitor cells of such cells. The chondrocytes may be cells expressing chondrocyte markers, for example, type II collagen (COL2A1) and SOX9. The COL2A1 herein includes human COL2A1 genes having the nucleotide sequences of NCBI accession numbers NM_001844 and NM_033150, mouse COL2A1 genes having the nucleotide sequences of NCBI accession numbers NM_001113515 and NM_031163, proteins encoded by the genes, and naturally occurring variants having the same functions as those of the genes or the proteins. The SOX9 herein includes a human SOX9 gene having the nucleotide sequence of NCBI accession number NM_000346, a mouse SOX9 gene having the nucleotide sequence of NCBI accession number NM_011448, proteins encoded by the genes, and naturally occurring variants having the same functions as those of the genes or the proteins. The chondrocytes produced in the present invention may be produced in a cell population containing chondrocytes and other types of cells. The chondrocytes in the cell population account for, for example, 70% or more, 80% or more, 90% or more, 95% or more, or 98% or more of the total cells. The chondrocytes obtained by the method of the present invention may be obtained as a cartilaginous tissue (also called a cartilaginous particle) containing chondrocytes and an extracellular matrix. The cartilaginous tissue is composed of an outer membrane and inner components surrounded by the outer membrane. The outer membrane comprises COL1 fibers but no COL2 fibers and has a thickness of 10 to 50 μm. The inner components comprise COL11 fibers, COL2 fibers, proteoglycans and chondrocytes. The COL1 fibers herein are fibers having a triple helix structure formed of proteins encoded by the COL1 gene. The COL2 fibers herein are fibers having a triple helix structure formed of proteins encoded by the COL2 gene. The COL11 fibers herein are fibers having a triple helix structure formed of proteins encoded by the COL11 gene. The proteoglycans herein is a group of compounds in which polysaccharides composed of repeating disaccharide units (such as chondroitin sulfate) are linked to amino acid (serine) residues on a core protein via saccharides (xylose, galactose and/or glucuronic acid).

(i) Step of Culturing Pluripotent Stem Cells Under Adherent Conditions in a Medium Containing an HMG-CoA Reductase Inhibitor and One or More Substances Selected from the Group Consisting of BMP2, TGFβ and GDF5

The medium used in step (i) can be prepared by adding an HMG-CoA reductase inhibitor and one or more substances selected from the group consisting of BMP2, TGFβ and GDF5 to a basal medium for animal cell culture. A preferable medium used in step (i) is a basal medium supplemented with BMP2, TGFβ, GDF5 and an HMG-CoA reductase inhibitor. Examples of the basal medium include IMDM, Medium 199, Eagle's minimum essential medium (EMEM), αMEM, Dulbecco's modified Eagle's medium (DMEM), Ham's F12 medium, RPMI 1640 medium, Fischer's medium and a mixed medium thereof. As needed, the basal medium may contain an additional ingredient such as serum (e.g., FBS), albumin, transferrin, KnockOut Serum Replacement (KSR) (serum substitute for FBS in ES cell culture) (Invitrogen), N2 supplement (Invitrogen), B27 supplement (Invitrogen), fatty acids, insulin, sodium selenite, ethanolamine, collagen progenitors, trace elements, 2-mercaptoethanol, 3'-thiolglycerol, lipids, amino acids, L-glutamine, GlutaMAX (Invitrogen), non-essential amino acids (NEAAs), sodium pyruvate, vitamins, growth factors, low-molecular-weight compounds, antibiotics, antioxidants, pyruvic acid, buffering agents and inorganic salts. In one embodiment of this step, the basal medium is DMEM containing insulin, transferrin, sodium selenite, ethanolamine, ascorbic acid, non-essential amino acids, sodium pyruvate, antibiotics and 1% serum.

The BMP2 in step (i) includes human BMP2, non-human BMP2 and functionally modified derivatives thereof. The BMP2 may be, for example, a commercially available product from Osteopharma etc. The concentration of BMP2 used in this step is 0.1 to 1000 ng/mL, preferably 1 to 100 ng/mL, more preferably 5 to 50 ng/mL, in particular 10 ng/mL. BMP2 may be replaced with BMP4 in the present invention.

The TGFβ in step (i) includes human TGFβ, non-human TGFβ and functionally modified derivatives thereof. The TGFβ may be, for example, a commercially available product from PeproTech etc. The concentration of TGFβ used in this step is 0.1 to 1000 ng/mL, preferably 1 to 100 ng/mL, more preferably 5 to 50 ng/mL, in particular 10 ng/mL.

The GDF5 in step (i) includes human GDF5, non-human GDF5 and functionally modified derivatives thereof. The GDF5 may be, for example, a commercially available product from PeproTech etc. The concentration of GDF5 used in this step is 0.1 to 1000 ng/mL, preferably 1 to 100 ng/mL, more preferably 5 to 50 ng/mL, in particular 10 ng/mL.

Examples of the HMG-CoA reductase inhibitor used in the present invention include, but are not limited to, mevastatin (compactin) (see U.S. Pat. No. 3,983,140), pravastatin (see JP-A 57-2240 (U.S. Pat. No. 4,346,227)), lovastatin (see JP-A 57-163374 (U.S. Pat. No. 4,231,938)), simvastatin (see JP-A 56-122375 (U.S. Pat. No. 4,444,784)), fluvastatin (see JP-W 60-500015 (U.S. Pat. No. 4,739,073)), atorvastatin (see JP-A 3-58967 (U.S. Pat. No. 5,273,995)), rosuvastatin (see JP-A 5-178841 (U.S. Pat. No. 5,260,440)) and pitavastatin (see JP-A 1-279866 (U.S. Pat. Nos. 5,854,259 and 5,856,336)). The HMG-CoA reductase inhibitor used in the present invention is preferably selected from the group consisting of mevastatin, atorvastatin, pravastatin, rosuvastatin, fluvastatin and lovastatin.

When rosuvastatin is used as the HMG-CoA reductase inhibitor in step (i), the concentration is 0.01 µM to 100 µM, preferably 0.1 µM to 10 µM, more preferably 0.5 µM to 5 µM, in particular 1 µM.

In step (i), the basal medium may be further supplemented with bFGF. The bFGF includes human bFGF, non-human bFGF and functionally modified derivatives thereof. The bFGF may be, for example, a commercially available product from WAKO etc. The concentration of bFGF used in this step is 0.1 to 1000 ng/mL, preferably 1 to 100 ng/mL, more preferably 5 to 50 ng/mL, in particular 10 ng/mL.

In step (i), the basal medium may be further supplemented with a pterosin derivative. The pterosin derivative is, for example, the same as described in Ser. No. 14/315,809, preferably pterosin B. The concentration of pterosin B used in this step is 10 µM to 1000 µM, preferably 100 µM to 1000 µM.

In the present invention, "culturing under adherent conditions" refers to culturing cells in a state in which the cells are allowed to adhere on a culture dish. This can be performed by culturing cells using a culture vessel having a surface treated for cell adhesion. The surface-treated culture vessel may be a commercially available product, for example, a tissue culture dish available from IWAKI. In another embodiment, culturing under adherent conditions is performed using a culture vessel coated with an extracellular matrix. The coating treatment can be achieved by adding a solution containing an extracellular matrix to a culture vessel, followed by removing the solution at an appropriate timing.

The extracellular matrix herein is a supramolecular assembly present outside the cells, and may be naturally occurring or artificial (recombinant). Examples of the extracellular matrix include polylysine, polyornithine, collagens, proteoglycans, fibronectins, hyaluronic acid, tenascins, entactins, elastins, fibrillins, laminins and fragments of these substances. These extracellular matrices may be used in combination as needed.

The culture temperature in step (i) is not particularly limited, and is for example, about 30 to 40° C., preferably about 37° C. The culture is performed under an atmosphere of air with $CO_2$. The $CO_2$ concentration is about 2 to 5%, preferably about 5%. The culture period in this step is, for example, 7 days to 28 days, 10 days to 25 days or 10 days to 20 days, and is preferably 14 days.

(ii) Step of Culturing the Cells Obtained in Step (i) Under Suspension Conditions in a Medium Containing an HMG-CoA Reductase Inhibitor and One or More Substances Selected from the Group Consisting of BMP2, TGFβ and GDF5

Step (ii) can be performed by detaching the cells obtained in step (i) from the culture vessel and culturing the cells in suspension. The detachment of the cultured cells in step (ii) is preferably achieved by mechanical means (e.g., pipetting or using a scraper etc.), not using a detachment solution with protease activity and/or collagenase activity (e.g., solutions containing trypsin and collagenase, such as Accutase™ and Accumax™ (Innovative Cell Technologies, Inc.)).

"Culturing under suspension conditions" in the method of the present invention refers to culturing cells in a state in which the cells are not adherent to a culture dish. This can be performed in various ways without particular limitation, and is preferably performed using a culture vessel (e.g., a Petri dish) without artificial treatment for enhancing cell adhesion to the vessel (e.g., coating treatment using an extracellular matrix etc.) or a culture vessel with artificial treatment for preventing cell adhesion to the vessel (e.g., coating treatment using polyhydroxyethyl methacrylate (poly-HEMA)).

The medium used in step (ii) may be the same as described above in step (i).

The culture temperature in step (ii) is not particularly limited, and is for example, about 30 to 40° C., preferably about 37° C. The culture is performed under an atmosphere of air with $CO_2$. The $CO_2$ concentration is about 2 to 5%, preferably about 5%. The culture period in this step is, for example, 7 days to 28 days, 10 days to 25 days or 10 days to 20 days, and is preferably 14 days. The culture is desirably continued until chondrocytes are obtained. The culture period can be optimized by monitoring chondrogenic differentiation. The chondrogenic differentiation in the present invention can be examined by sampling part of the obtained cartilaginous particles and subjecting them to safranin O staining.

The present invention provides a pharmaceutical product comprising chondrocytes obtained by the method described above. The administration of the pharmaceutical product to a patient can be performed, for example, as follows. The culture products (cartilaginous particles) composed of chondrocytes obtained by the above method and an extracellular matrix from the chondrocytes are glued with a fibrin glue to form a construct of an appropriate size for the administration site. The construct is administered into the patient's cartilage defect site. Alternatively, the cartilaginous particles are mixed with a gelatin gel, a collagen gel, a hyaluronic acid gel and/or the like, and administered into the defect site. Alternatively, the cartilaginous particles are administered into the defect site and fixed with periosteum etc.

Examples of the diseases to be treated with the pharmaceutical product include defects of facial cartilage, such as nasal cartilage and auricular cartilage, and defects of articular cartilage. The pharmaceutical product is preferably used for treatment of articular cartilage injury.

In the present invention, the number of the chondrocytes or the cartilaginous particles contained in the pharmaceutical product is not particularly limited as long as engraftment of the transplant is successfully achieved. The number of the chondrocytes or the cartilaginous particles may be increased or decreased as appropriate for the size of the defect site or the body size of the patient.

The present invention will be described more specifically with reference to Examples below, but the present invention is not limited thereto.

EXAMPLES

Example 1

Human iPS Cells

The 1231A3 cell line, which was established by the method described in Nakagawa M, et al., Sci Rep. 4:3594 (2014), was provided from the Center for iPS Cell Research and Application, Kyoto University, and was used as human iPS cells.

The human iPS cells were incubated with 0.5×TrypLE Select, and then detached using a cell scraper. The number of the cells was counted, and $1.0 \times 10^6$ to $2.0 \times 10^6$ cells were transferred to a 30-mL bioreactor (BWV-S03A, ABLE Corporation). To the bioreactor, 30 mL of StemFit AK03 (Ajinomoto) supplemented with 10 nM Y-27632 (Wako) was added, and the cells were cultured under the conditions of 37° C. and 5% $CO_2$ for 5 days with stirring using a 6-ch magnetic stirrer (BWS-S03NOS-6, ABLE Corporation) at a rotation speed of 55 rpm. As a result, iPS cell clusters of 50 to 300 μm in diameter were obtained.

Chondrogenic Induction

The iPS cell clusters obtained by the above method were collected, and the whole or half of them were seeded on a 10-cm culture dish (Iwaki) with 5 mL of chondrogenic differentiation medium. The chondrogenic differentiation medium used was DMEM (SIGMA) supplemented with 1% FBS (Invitrogen), 1% ITS-X (Invitrogen), 50 μg/mL ascorbic acid (Nakalai), non-essential a.a. (Invitrogen), sodium pyruvate (Invitrogen), 10 ng/mL BMP2 (Astellas), 10 ng/mL TGF-β1 (PeproTech), 10 ng/mL GDF5 (J&J), 1 μM rosuvastatin (BioVision), penicillin & streptomycin (Invitrogen) and plasmocin (InvivoGen). After seeding, the iPS cell clusters were cultured under the conditions of 37° C. and 5% $CO_2$. After 2 or 3 days, the chondrogenic differentiation medium was changed to a fresh one. Afterwards, medium change was performed at intervals of 2 to 5 days during 2 weeks of the culture. During the culture period, the iPS cell clusters gradually adhered on the dish and ultimately formed nodules.

The formed nodules were detached using a cell scraper, transferred to a 10-cm Petri dish, and cultured under the conditions of 37° C. and 5% $CO_2$. After 2 or 3 days, the chondrogenic differentiation medium was changed to a fresh one. Afterwards, medium change was performed every 3 to 7 days. At the time of medium change, if there were nodules stuck to the dish, they were detached using a cell scraper and suspended in the medium. Cell clusters obtained 28 days from the start of differentiation induction, i.e., culture in chondrogenic differentiation medium, were examined by safranin O staining.

The results show that cell clusters (cartilaginous particles) intensely stained with safranin O, i.e., cell clusters composed of an extracellular matrix and chondrocytes were obtained (FIG. 1).

Figure 2:
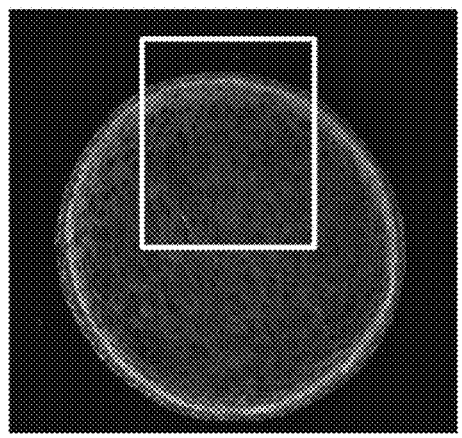
FIG. 2 shows the results of double immunofluorescence staining for type I and II collagens in a particle harvested after 70 days of differentiation induction of human iPS cell clusters in chondrogenic differentiation medium and in a mouse embryonic cartilage primordium.
Figure 2:
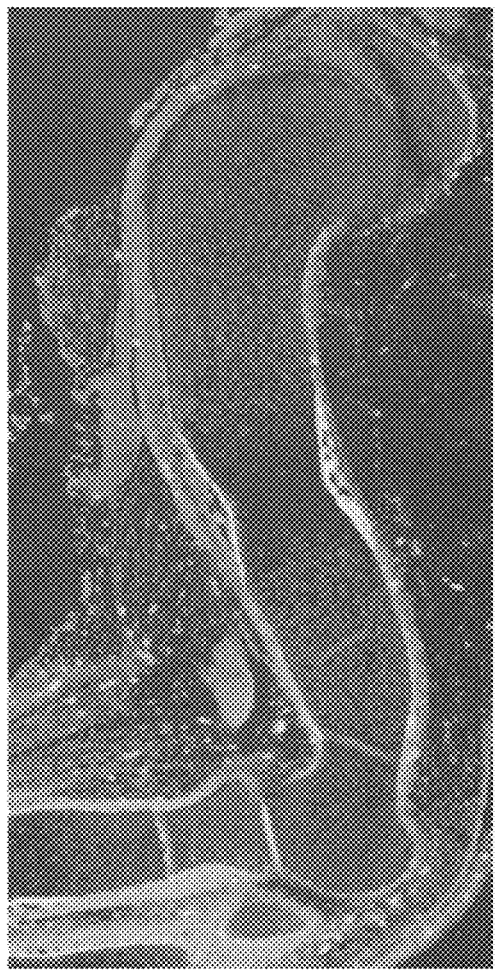

Separately, cell clusters (hereinafter called "human iPS cell-derived cartilaginous particles") obtained 70 days from the start of the differentiation induction were examined by double immunofluorescence staining for type I and II collagens. For comparison, the cartilage primordia of the humerus of a mouse embryo (14.5-day embryo) were prepared as specimens and also subjected to double immunofluorescence staining for type I and II collagens. As a result, both in the human iPS cell-derived cartilaginous particles and in the mouse embryonic cartilage primordia, a type II collagen-positive cartilage tissue was surrounded by a type I collagen-positive membrane as shown in FIG. 2. The surrounding membrane of the cartilage primordium is called perichondrium. The results show that the human iPS cell-derived cartilaginous particles are morphologically similar to the embryonic cartilage consisting of cartilage and perichondrium.

Example 2

Human iPS Cells

The 1231A3 cell line, which was established by the method described in Nakagawa M, et al., Sci Rep. 4:3594 (2014), was provided from the Center for iPS Cell Research and Application, Kyoto University, and was used as human iPS cells.

The human iPS cells were incubated with 0.5×TrypLE Select, and then detached using a cell scraper. The number of the cells was counted, and $0.5 \times 10^7$ to $1.0 \times 10^7$ cells were transferred to a 100-mL bioreactor (BWV-S10A, ABLE Corporation). To the bioreactor, 100 mL of StemFit AK02N (Ajinomoto) supplemented with 10 nM Y-27632 (Wako) was added, and the cells were cultured under the conditions of 37° C. and 5% $CO_2$ for 4 to 7 days with stirring using a magnetic stirrer (BWS-S03NOS-6, ABLE Corporation) at a rotation speed of 60 rpm. As a result, iPS cell clusters of 50 to 300 μm in diameter were obtained.

Chondrogenic Induction

The iPS cell clusters obtained by the above method were collected and seeded on four to twelve 10-cm suspension culture dishes (Sumitomo) with 5 mL of chondrogenic differentiation medium. The chondrogenic differentiation medium used was DMEM (SIGMA) supplemented with 1% FBS (Invitrogen), 1% ITS-X (Invitrogen), 50 μg/mL ascorbic acid (Nakalai), non-essential a.a. (Invitrogen), sodium pyruvate (Invitrogen), 10 ng/mL BMP2 (PeproTech), 10 ng/mL TGF-β1 (PeproTech), 10 ng/mL GDF5 (J&J), 1 μM rosuvastatin (BioVision), penicillin & streptomycin (Invitrogen) and plasmocin (InvivoGen). After seeding, the iPS cell clusters were cultured under the conditions of 37° C. and 5% $CO_2$. After 1 to 5 days, the chondrogenic differentiation medium was changed to a fresh one. Afterwards, medium change was performed at intervals of 2 to 7 days during 2 to 3 weeks of the culture. During the culture period, the iPS cell clusters gradually adhered on the dishes and ultimately formed nodules.

The formed nodules were detached using a cell scraper, transferred to a 6-cm suspension culture dish (Sumitomo), and cultured under the conditions of 37° C. and 5% $CO_2$. After 1 to 3 days, the chondrogenic differentiation medium was changed to a fresh one. Afterwards, medium change was performed every 2 to 7 days. At the time of medium change, if there were nodules stuck to the dish, they were detached using a cell scraper and suspended in the medium. Cell clusters obtained 28 days from the start of differentiation induction, i.e., culture in chondrogenic differentiation medium, were examined by safranin O staining.

The results show that cell clusters (cartilaginous particles) intensely stained with safranin O, i.e., cell clusters composed of an extracellular matrix and chondrocytes were obtained.

Example 3

Human iPS Cells

The Ff-I01 cell line, which was established by the method described in Nakagawa M, et al., Sci Rep. 4:3594 (2014), was provided from the Center for iPS Cell Research and Application, Kyoto University, and was used as human iPS cells.

The human iPS cells were incubated with 0.5×TrypLE Select, and then detached using a cell scraper. The number of the cells was counted, and $0.5 \times 10^7$ to $1.0 \times 10^7$ cells were transferred to a 100-mL bioreactor (BWV-S10A, ABLE Corporation). To the bioreactor, 100 mL of StemFit AK03N (Ajinomoto) supplemented with 10 nM Y-27632 (Wako) was added, and the cells were cultured under the conditions of 37° C. and 5% $CO_2$ for 4 to 7 days with stirring using a magnetic stirrer (BWS-S03NOS-6, ABLE Corporation) at a rotation speed of 60 rpm. As a result, iPS cell clusters of 50 to 300 μm in diameter were obtained.

Chondrogenic Induction

The iPS cell clusters obtained by the above method were collected and seeded on four to twelve 10-cm suspension culture dishes (Sumitomo) with 5 mL of chondrogenic differentiation medium. The chondrogenic differentiation medium used was DMEM (SIGMA) supplemented with 0.2% FBS (Invitrogen), 1% ITS-X (Invitrogen), 50 μg/mL ascorbic acid (Nakalai), non-essential a.a. (Invitrogen), sodium pyruvate (Invitrogen), 10 ng/mL BMP2 (PeproTech), 10 ng/mL TGF-β3 (Wako), 10 ng/mL GDF5 (BioVision) and 1 μM rosuvastatin (BioVision). After seeding, the iPS cell clusters were cultured under the conditions of 37° C. and 5% $CO_2$. After 1 to 3 days, the chondrogenic differentiation medium was changed to a fresh one. Afterwards, medium change was performed at intervals of 2 to 5 days during 2 to 3 weeks of the culture. During the culture period, the iPS cell clusters gradually adhered on the dishes and ultimately formed nodules.

The formed nodules were detached using a cell scraper, transferred to a 6-cm suspension culture dish (Sumitomo), and cultured under the conditions of 37° C. and 5% $CO_2$. After 1 to 5 days, the chondrogenic differentiation medium was changed to a fresh one. Afterwards, medium change was performed every 2 to 7 days. At the time of medium change, if there were nodules stuck to the dish, they were detached using a cell scraper and suspended in the medium. Cell clusters obtained 56 days from the start of differentiation induction, i.e., culture in chondrogenic differentiation medium, were examined by safranin O staining.

The results show that cell clusters (cartilaginous particles) intensely stained with safranin O, i.e., cell clusters composed of an extracellular matrix and chondrocytes were obtained.

Example 4

Figure 3:
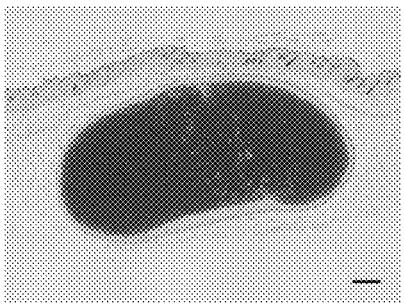
FIG. 3 shows the results of tissue observation around the transplantation site in SCID mice at 3 and 12 months after transplantation of particles harvested after 42 days of differentiation induction of human iPS cell clusters in chondrogenic differentiation medium.
Figure 3:
Figure 3:
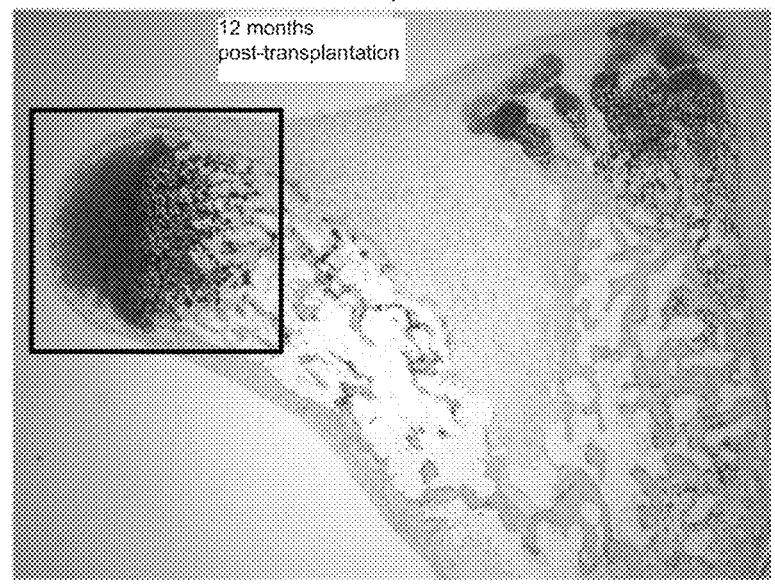
Figure 3:
Figure 3:
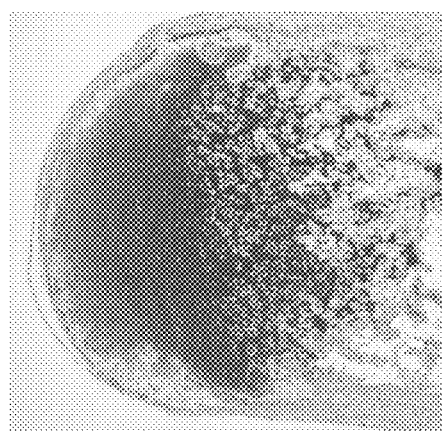
Figure 3:
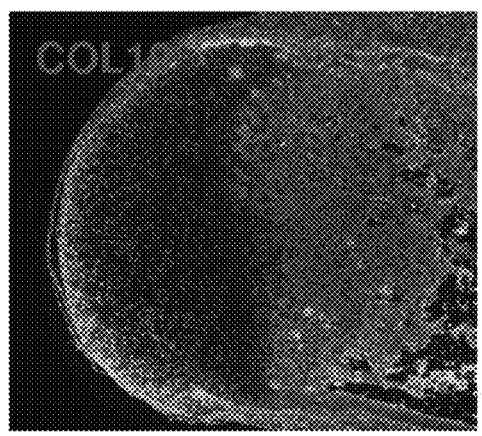

Human iPS cell-derived cartilaginous particles obtained 42 days from the start of the differentiation induction in Example 1 were subcutaneously transplanted into SCID mice (C.B-17/Icr-scid/scid Jcl). Three and twelve months after the transplantation, the tissue around the transplantation site was excised from the mice, and tissue specimens were prepared according to the usual method and subjected to histological analysis. As a result, it was shown that a cartilage-bone tissue-cartilage structure was formed around the transplantation site at 12 months post transplantation as shown in FIG. 3. This indicates that the human iPS cell-derived cartilage subcutaneously transplanted into the mice underwent endochondral ossification. As shown in the magnified image, chondrocytes in the region of the cartilage-to-bone tissue transition were enlarged, and the matrix surrounding these chondrocytes expressed type X collagen. The enlargement and the type X collagen expression are the hallmarks of hypertrophic chondrocytes, and therefore, the chondrocytes in that region are hypertrophic chondrocytes. The presence of hypertrophic chondrocytes supports the occurrence of endochondral ossification.

The potential of human iPS cell-derived cartilaginous particles to undergo endochondral ossification, the morphological similarity shown in FIG. 2, and the functional similarity shown in FIG. 3 indicate that human iPS cell-derived cartilaginous particles are equivalent to embryonic cartilage primordia.

Example 5

Figure 4:
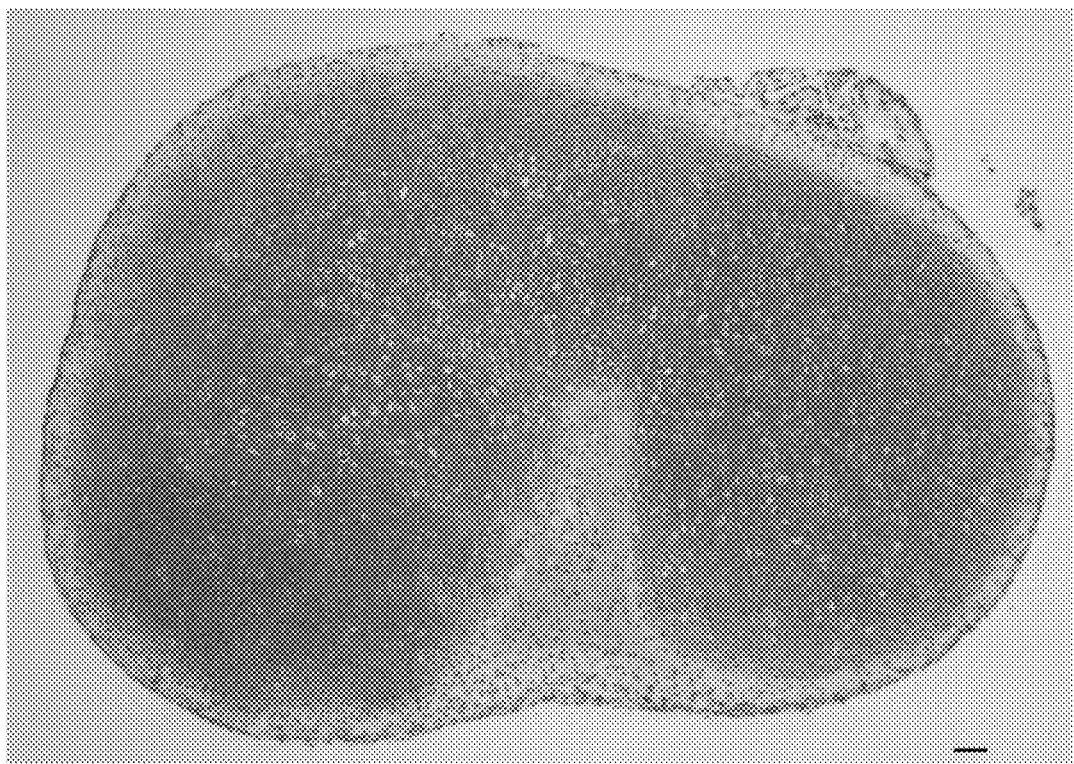
FIG. 4 shows the image of two particles which were harvested after 90 days of differentiation induction of human iPS cell clusters in chondrogenic differentiation medium and then cultured in contact with each other for 60 days.

Two human iPS cell-derived cartilaginous particles obtained 90 days after the start of the differentiation induction in Example 1 were cultured in contact with each other in medium for 60 days. As a result, the two particles were integrated to form a single particle as shown in FIG. 4. Originally, the two particles were independent cartilage tissues surrounded by their respective perichondria, but in the integrated part, the perichondria disappeared and the cartilage tissues started integrating with each other.

In regenerative medicine for cartilage, a plurality of cartilaginous particles are transplanted into the cartilage defect site of a patient or an animal model. The repair of the tissue around the transplantation site requires integration between the cartilaginous particles as well as between the cartilaginous particles and the cartilage in the graft bed. The human iPS cell-derived cartilaginous particles obtained by the present invention are shown to integrate with each other in vitro, and therefore are highly expected to integrate in vivo after transplantation, resulting in effective repair.

The invention claimed is:

1. A method for producing chondrocytes from pluripotent stem cells, the method comprising:
   (i) culturing pluripotent stem cells under adherent conditions in a medium containing an HMG-CoA reductase inhibitor and one or more substances selected from the group consisting of BMP2, TGFβ and GDF5, and
   (ii) culturing the cells obtained in step (i) under suspension conditions in a medium containing an HMG-CoA reductase inhibitor and one or more substances selected from the group consisting of BMP2, TGFβ and GDF5, wherein the pluripotent stem cells used in step (i) are in the form of cell clusters produced by a method comprising suspension culture in a medium that allows the pluripotent stem cells to retain their undifferentiated state.

2. The method according to claim 1, wherein the medium used in steps (i) and (ii) is a medium containing BMP2, TGFβ, GDF5 and a HMG-CoA reductase inhibitor.

3. The method according to claim 1, wherein the HMG-CoA reductase inhibitor is selected from the group consisting of mevastatin, atorvastatin, pravastatin, rosuvastatin, fluvastatin and lovastatin.

4. The method according to claim 3, wherein the HMG-CoA reductase inhibitor is rosuvastatin.

5. The method according to claim 1, wherein the medium used in steps (i) and (ii) further comprises serum.

6. The method according to claim 1, wherein step (ii) comprises culturing the cells obtained in step (i) in a suspension without use of a detachment solution with protease activity and/or collagenase activity.

7. The method according to claim 1, wherein the chondrocytes are in the form of clusters, which comprise the chondrocytes and an extracellular matrix.

8. The method according to claim 1, wherein steps (i) and (ii) are each conducted over a period of 7 to 28 days.

9. The method according to claim 8, wherein steps (i) and (ii) are each conducted over a period of 14 days.

* * * * *